United States Patent [19]

Ogawa et al.

[11] Patent Number: 4,737,258

[45] Date of Patent: Apr. 12, 1988

[54] ELEMENT FOR ELECTROPHORESIS CONTAINING POLYACRYLAMIDE GEL MEMBRANE

[75] Inventors: Masashi Ogawa, Asaka; Masafumi Fukugawa, Minami-Ashigara; Teppei Ikeda, Asaka, all of Japan

[73] Assignee: Fuji Photo Film Co., Ltd., Kanagawa, Japan

[21] Appl. No.: 734,036

[22] Filed: May 14, 1985

[30] Foreign Application Priority Data

May 14, 1984 [JP] Japan .................................. 59-96152
May 14, 1984 [JP] Japan .................................. 59-96153

[51] Int. Cl.$^4$ .............................................. B01D 57/02
[52] U.S. Cl. ............................... 204/299 R; 204/182.8; 428/479.3
[58] Field of Search ................. 204/299 R, 182.8; 524/555, 215, 210, 423, 35, 850, 732, 726, 714, 745; 428/474.4, 532, 326, 327, 479.3, 476.3, 476.9, 481, 482, 483; 210/635

[56] References Cited

U.S. PATENT DOCUMENTS 4,415,428 11/1983 Nochumson et al. .......... 204/299 R
4,548,869 10/1985 Ogawa et al. ................ 204/182.8 X

FOREIGN PATENT DOCUMENTS 212750 12/1984 Japan ................................ 204/182.8

Primary Examiner—John F. Niebling
Assistant Examiner—W. T. Leader
Attorney, Agent, or Firm—Jules E. Goldberg

[57] ABSTRACT

An element for electrophoresis suitably employable for electrophoresis of biopolymers such as proteins, as well as for determination of base sequence of DNA, RNA, their fragments, and their derivatives, which comprises a plastic support, an adhesive layer containing a cellulose derivative, and an electrophoresis medium layer comprising an aqueous polyacrylamide gel formed by crosslinking polymerization of an acrylamide compound and a crosslinking agent in the presence of water, which are superposed in this order. The electrophoresis medium layer may contain a water-soluble polymer and agarose. The medium layer may contain a modifier such as an anionic surfactant, formamide or urea.

9 Claims, No Drawings

ELEMENT FOR ELECTROPHORESIS CONTAINING POLYACRYLAMIDE GEL MEMBRANE

BACKGROUND OF THE INVENTION

1. Field of the Invention

This invention relates to an element for electrophoresis, and more particularly relates to an element for electrophoresis suitable employable for electrophoresis of biopolymers such as proteins, as well as for determination of base sequence of DNA, RNA, their fragments, and their derivatives.

2. Description of Prior Arts

For the analysis of biopolymers such as proteins, the electrophoresis can be carried out in the following manner.

A membrane medium for electrophoresis prepared by coating or casting a membrane-forming material such as agar, cellulose, cellulose acetate, starch, silica gel or polyacrylamide gel over a support such as a glass plate or a transparent plastic sheet (or film) is impregnated with a buffer solution; on the medium is applied a substance to be analyzed (sample); the applied sample is developed (or resolved) on or in the medium by applying a voltage between the both ends of the support and dyed thereon; and then the dyed sample is measured on the optical density to quantitavely determine the developed components of the sample.

Details of the electrophoresis and medium therefor are given in "Experimental Text for Electrophoresis (5th revision)" editted by Electrophoresis Society of Japan (Bunkodo, 1975), "Modern Electrophoresis" editted by Aoki & Nagai (Hirokawa Shoten, 1973), etc.

Recently, the electrophoresis has been employed to analyze substances originating from a living body; for instance, the analyses of proteins originating from a living body are generally performed in the course of biochemical analysis for diagnosis.

As the membrane or sheet for electrophoresis, a filter paper was previously employed, but recently an agarose membrane or a polyacrylamide gel membrane (or medium) has been employed from the viewpoints of their advantageous properties. Particularly, the polyacrylamide gel membrane showing a molecular sieve function is widely employed recently. The polyacrylamide gel membrane can be prepared by crosslinking polymerization of a monomer such as acrylamide and a two-functional crosslinking agent such as N,N′-methylenebisacrylamide under an oxygen-free condition in the presence of water and a polymerization catalyst.

In the course of the preparation of the polyacrylamide gel membrane, a modifier such as an anionic surfactant is incorporated into the membrane in certain cases. Since only a small amount of the modifier is required for the preparation of the gel membrane for protein analysis, the modifier can be incorporated into the membrane by applying an aqueous modifier solution onto the wet gel membrane or immersing the gel membrane in an aqueous modifier solution.

Since the polymerization reaction for the preparation of polyacrylamide is a radical crosslinking polymerization as described above, the polymerization can be easily inhibited by the presence of oxygen. Therefore, the gel membrane should be prepared in the absence of oxygen. For this reason, a polyacrylamide gel membrane is generally prepared by a process involving: introducing an aqueous solution (gel-forming solution or gel solution) containing acrylamide, a crosslinking agent and a polymerization catalyst into a cell formed between two glass plates with a certain clearance (e.g., 0.3-1 mm); sealing the gel-forming solution from oxygen; and causing the crosslinking polymerization to prepare the desired gel membrane. This procedure employing glass plates are disadvantageous because the glass plate is easily breakable and rather heavy and careful handling is accordingly required. Thus, the above procedure employing the glass plates is difficultly utilized to prepare the polyacrylamide gel membrane in a mass scale.

For the reason described above, it has been desired that the glass plate for supporting the polyacrylamide gel membrane is replaced with a light-weight plastic material support. However, for the use of a satisfactorily acceptable plastic material support such as a polyethylene terephthalate (PET) sheet, poor adhesion between the gel membrane and the plastic material support should be improved, for the reasons given below.

The prepared polyacrylamide gel is horizontally or vertically placed for performing slab electrophoresis. The electrophoresis is performed for a certain period of time under predetermined conditions, and the desired analysis of the components originating from the living body is done after dyeing the electrophoresed gel membrane with, for instance, Ponceau 3R (Ciba-Geigy), Coomassie Brilliant Blue G-250 (ICI), or silver. The gel membrane is apt to separate from the support in the dyeing procedure even in the case of employing the glass plate support. Therefore, the dyeing procedure requires highly skilled operation to prevent the separation of the gel membrane from the support. The poor affinity of the plastic material support to the polyacrylamide gel membrane makes it more difficult to handle the element for electrophoresis without separation of the support from the gel membrane.

In the method for determination of base sequence of DNA, RNA, their fragments, and their derivatives according to the post-label method, the procedure of slab electrophoresis using a polyacrylamide gel membrane has become essential. Since the study in the genetic engineering technology has advance recently, quick determination of the base sequence of DNA, etc, is highly desired.

The polyacrylamide gel membrane employable for the above purpose also can be prepared by crosslinking polymerization of a monomer such as acrylamide and a two-functional crosslinking agent such as N,N′-methylenebisacrylamide under an oxygen-free condition in the presence of water and a polymerization catalyst. In the course of the preparation of the polyacrylamide gel membrane, a modifier such as urea or formamide is generally incorporated into the membrane.

The polyacrylamide gel membrane prepared as above is employed for electrophoresis in the manner such as described below.

The polyacrylamide gel membrane is vertically placed in the form of being sandwiched between the glass plates, and in the first place a pre-electrophoresis procedure is carried out. Then, a certain amount of a sample ($^{32}$P-labeled DNA cleaved by Maxam-Gilbert method) is introduced into sample slots provided on the membrane, and electrophoresis is carried out. After the electrophoresis is carried out for a certain period of time (e.g., approx. 6-12 hours), one glass plate is removed carefully. Then, the exposed gel membrane is covered with a polymer film such as a poly(vinylidene chloride) film and subjected to the autoradiographic process. The autoradiographic process is carried out by the following procedures: A radiographic film and an intensifying screen are superposed successively on the film covering the gel membrane, whereby exposing the radiographic film to the gel membrane at a low temperature (e.g., −80° C.) for a certain period of time (e.g., approx. 10–20 hours). After the exposing procedure, the radiographic film is developed, and the resolved pattern reproduced on the film is studied for determination of the base sequence of DNA, etc.

Since the autoradiographic process requires a long period as described above, it has been desired that the operational period is shortened. Moreover, enhancement of resolution accuracy in the detection of the resolved pattern is desired.

It is known that the resolution accuracy can be enhanced by applying the autoradiographic process to the gel membrane in dry state. The procedure for drying the gel membrane can be carried out as follows. The gel membrane having been subjected to electrophoresis is immersed in 10% aqueous acetic acid solution so as to fix the resolved DNA cleavage products as well as to remove the modifier such as urea from the membrane. The adhesion between the glass plate and the gel membrane is weak or negligible, the gel membrane easily separates from the glass plate and floats in the solution. The separated gel membrane is carefully taken out, placed on a filter paper, and dried under reduced pressure. The membrane is thus dried and fixed onto the filter paper. The autoradiographic process applied to the dry membrane shows highly enhanced resolution. However, the drying process has such drawbacks that the separation and drying stages require highly trained skill and careful handling and actually the membrane is sometimes broken in these stages.

SUMMARY OF THE INVENTION

An object of the present invention is to provide a element for electrophoresis which is improved in the adhesion between the support and the aqueous gel medium such as in the form of a membrane under wet condition.

Another object of the present invention is to provide a element for electrophoresis which is substantially free from sepration of the aqueous gel medium layer from the support in the following stages such as post-treatment stage in an aqueous solution and a subsequent drying stage.

There is provided by the present invention an element for electrophoresis comprising:
(I) a plastic material support;
(II) an adhesive layer containing a cellulose derivative; and
(III) a medium layer for electrophoresis comprising an aqueous polyacrylamide gel formed by crosslinking polymerization of an acrylamide compound and a crosslinking agent in the presence of water,
which are superposed in this order.

The element for electrophoresis of the invention comprises the three-layers structure of a support layer, an adhesive layer containing a cellulose derivative, and an electrophoresis medium layer. Such three-layers structure is highly resistant to separation between the support layer and the electrophoresis medium layer in a variety of stages. Accordingly, the medium layer is hardly broken in the analytical procedure, and the handling of the element is satisfactorily easy.

Moreover, the electrophoresis element of the present invention can be prepared by forming the electrophoresis layer on a holizontally arranged adhesive layer-covered support. Therefore, the element for electrophoresis of the invention can be advantageously prepared in a mass scale.

DETAILED DESCRIPTION OF THE INVENTION

Examples of the support employable for the preparation of the element for electrophoresis of the present invention include a variety of polymer materials in the form of sheet (the term "sheet" includes a film and a plate). Examples of the polymer materials include polyethylene terephthalate, polycarbonate of Bisphenol A, polyvinyl chloride, vinylidene chloride-vinyl chloride copolymer, polymethyl methacrylate, polyethylene, polypropylene, cellulose acetates, and cellulose acetate propionate. Preferred is a polyethylene terephthalate sheet.

The support employed in the invention can be subjected to glow discharge treatment prior to the provision of the adhesive layer containing a cellulose derivative thereon.

The glow discharge treatment can be applied onto the support under such conditions that the surface of the support can be made hydrophilic. The glow discharge treatment for making a surface of a polymer material hydrophilic is already known. Accordingly, such known arts can be applied for the glow discharge treatment of the support.

The glow discharge treatment can be applied to another surface of the support. If the glow discharge treatment is applied to the reverse side surface, said surface can be advantageously combined with a glass plate without an adhesive in the case that the element for electrophoresis of the invention is to be tentatively arranged on a glass plate.

The support generally has a thickness in the range of approx. 50 to 500 μm, preferably approx. 70 to 300 μm.

On the support, the adhesive layer containing a cellulose derivative is provided.

There is no specific limitation on the cellulose derivative, as far as it is capable of forming a film. Preferred examples of the cellulose derivative include diacetylcellulose, triacetylcellulose and nitrocellulose. The cellulose derivative can be employed singly or in combination. Into the adhesive layer other polymers and additives can be incorporated, provided that the amount of these material is not more than 50 wt. %. Examples of the polymers and additives include gelatin, dextrane, polymethyl methacrylate, polyacrylamide, polyacrylic acid, polyvinyl alcohol, p-chlorophenol, resorcinol, glycerol and ethyleneglycol.

The cellulose derivative-containing adhesive layer preferably contains the cellulose additive in an amount of not less than 80 wt. %. More preferably, the adhesive layer consists essentially of the cellulose additive.

The adhesive layer may be a single layer or in the form of a composite layer of two or more layers. If the adhesive layer is in the form of a composite layer, a polymer layer can be combined with the cellulose derivative-containing layer. The polymer layer employable with the cellulose derivative-containing layer can be made of gelatin, polymethyl methacrylate, polyacrylamide, polyvinyl alcohol, polyvinylidene chloride.

The polymer layer can be placed between the support and the cellulose derivative-containing layer.

The adhesive layer may be a single layer or in the form of a composite layer of two or more layers. If the adhesive layer is in the form of a composite layer, a polymer layer can be combined with the cellulose derivative-containing layer. The polymer layer employable with the cellulose derivative-containing layer can be made of gelatin, polymethyl methacrylate, polyacrylamide, polyvinyl alcohol, polyvinylidene chloride. The polymer layer can be placed between the support and the cellulose derivative-containing layer.

The adhesive layer generally has a thickness of approx. 0.5 to 3 $\mu$m, preferably approx. 0.1 to 2 $\mu$m.

The aqueous gel medium layer is now described in more detail.

The aqueous gel medium (may be referred to herein as "gel membrane") employed in the invention is a medium layer consisting essentially of an aqueous polyacrylamide gel formed by crosslinking polymerization of an acrylamide compound and a crosslinking agent in the presence of water.

For the preparation of the polyacrylamide gel membrane, an acrylamide compound and a crosslinking agent are dissolved or dispersed in water to prepare an aqueous solution or an aqueous dispersion, in which the crosslinking reaction is carried out to form an aqueous polyacrylamide gel membrane. Hereinafter, the term "dissolving (in water)" means to include both "dissolving (in water)" and "dispersing (in water)", and the term "aqueous solution" means to include both "aqueous solution" and "aqueous dispersion", unless otherwise indicated. The term "aqueous medium" is used to include both a simple water as well as an aqueous mixture of water and an organic solvent, the organic solvent being optionally added.

Examples of the acrylamide compound employable in the present invention include acrylamide and its homologues such as N-methylacrylamide, N,N-dimethylacrylamide, N-(hydroxymethyl)acrylamide and diacetonacrylamide, as well as methacrylamide and its homologes. These compounds can be employed independently or in combination. Acrylamide is most preferred among these acrylamide compounds, and said acrylamide can be also preferably employed in combination with one or more of other acrylamide compounds.

As the crosslinking agent employable to obtain the polyacrylamide gel membrane, a known crosslinking agent described, for instance, in "Electrophoresis" 1981, 2, 213–228 can be employed singly or in combination. Examples of the crosslinking agent include bifunctional compounds such as N,N'-methylenebisacrylamide (BIS), N,N'-propylenebisacrylamide (PBA), di(acrylamide dimethyl)-ether (i.e., N,N'-oxydimethyleneacrylamide), 1,2-diacrylamide ethyleneglycol (DEG), 1,3-diacryloylethyleneurea, ethylene diacrylate (EDA), N,N'-diallyltartardiamide (DATD), and N,N'-bisacrylylcystamine (BAC). The crosslinking agent can be employed in the amount of approx. 2 to 30 wt. %, preferably approx. 3 to 10 wt. %, based on the total weight of the monomer (i.e., acrylamide compound) and the crosslinking agent. The gel concentration preferably is in the range of approx. 2 to 30 wt/v % (total weight of monomer and crosslinking agent per total volume of gel membrane comprising monomer, crosslinking agent and aqueous medium), the concentration being expressed in accordance with the diffinition indicated by S. Hjerten in Arch. Biochem. Biophys. 1 (Suppl.), 147 (1962).

The element for electrophoresis of the present invention can be employed for analysis of proteins and conjugated proteins (e.g., lipoproteins, glycoproteins, etc.) and the medium (gel membrane) of the element may comprise an anionic surfactant as a modifier. The use of the anionic surfactant is generally essential or preferable for the electrophoretic analyses of proteins or conjugated proteins, because it contributes to perform separation of the protein and conjugated protein and determination of molecular weight of these proteins. However, the medium of the element for electrophoresis may not contain the anionic surfactant.

Examples of the anionic surfactant include alkylsulfates, particularly alkylsulfates having a long chain alkyl group of at least 10 carbon atoms. The cation contained for formation of the salt generally is an alkali metal ion such as sodium ion, potassium ion, or lithium ion. Sodium ion is preferred from the economical viewpoint. The alkylsulfates preferably are dodecylsulfates (salts of sodium, potassium, lithium, etc.), and particularly preferred is sodium dodecylsulfate (SDS). The introduction of SDS into the gel membrane is particularly advantageous for separation of proteins and conjugated proteins, as well as for determination of molecular weight thereof. The anionic surfactant (modifier) can be contained in the gel-forming solution in the amount of approx. 0.05 to 2.0 wt/v % (weight per volume of the gel-forming solution), preferably approx. 0.1 to 1.5 wt/v %.

The element for electrophoresis of the invention also can be employed for determination of base sequence of DNA, RNA, their fragments, and their derivatives. For this purpose, a compound containing at least one carbamoyl group is generally incorporated into the electrophoresis medium as a modifier. Examples of the modifier include urea and formamide. Urea is most preferred. The modifier can be used in an amount of approx. 40 to 60 wt. % based on the volume of the aqueous gel containing the monomer and crosslinking agent. In the case that urea is used as the modifier, the amount generally ranges from approx. 6 moles (approx. 360 g.) per one liter of the aqueous gel containing the monomer and crosslinking agent to the saturation amount, preferably from approx. 7 moles (approx. 420 g.) to the saturation amount.

The gel membrane of the invention may contain an oxidation inhibitor. The oxidation inhibitor can be chosen from various compounds heretofore known as oxidation inhibitors employable for the gel membrane for electrophoresis. Examples of the oxidation inhibitor include 1,4-dithiothreitol and 2-mercaptoethanol.

The gel membrane of the invention may contain a water-soluble polymer. As the water-soluble polymer, a water-soluble polymer of the addition polymerization type or condensation polymerization type can be used. Examples of the polymer of the addition polymerization type include non-ionic water-soluble polymers such as polyvinyl alcohol, polyvinyl pyrrolidone, and polyacrylamide. Examples of polymer of the condensation polymerization type include non-ionic water-soluble polyalkylene glycols such as polyethylene glycol and polypropylene glycol. The water-soluble polymer of molecular weight ranging from approx. 10,000 to 1,000,000 is preferably used. Among these water-soluble polymers, polyacrylamide and polyethylene glycol are preferable. The water-soluble polymer is used in a range of approx. 2 to 100 wt. %, preferably, approx. 5 to 50 wt. %, based on the total weight of the monomer and crosslinking agent.

The addition of a water-soluble polymer serves to impart elasticity to the gel membrane, and thus modified gel membrane is still elastic even if it is dried. Thus, the gel membrane is so improved as to be free from brittleness, whereby the gel membrane becomes hardly breakable. Further, the viscosity of the gel membrane can be controlled by selecting the molecular weight and amount of the water-soluble polymer.

The gel membrane preferably contains agarose. There is no specific limitation on the agarose to be contained in the gel membrane, and any type of agarose such as low-electroendosmosis agarose, medium-electroendosmosis agarose, or high-electroendosmosis agarose can be used. Examples of agarose employable in the invention include agaroses disclosed in Japanese Patent Provisional Publication Nos. 55(1980)-5730, 55(1980)-110946 (corresponding to U.S. Pat. No. 4,290,911 and GB No. 2 042 571A), 57(1982)-502098 (WO No. 82/02599, U.S. Pat No. 4,319,976), etc. The amount of agarose to be added ranges from approx. 0.2 to 2 wt/v %, preferably from approx. 0.3 to 1.2 wt/v %, based on the volume of the aqueous gel containing the monomer and crosslinking agent. It becomes possible by the addition of agarose that the viscosity of the gel-forming solution can be controlled through changing the temperature of the solution, whereby suppressing flowability of the solution as well as facilitating the formation of the gel membrane.

A pH buffer agent can be contained in the gel membrane of the invention.

In the gel membrane of the element for electrophoresis of proten and protein derivatives, a buffer agent which is able to buffer a solution to a range of pH 2.5 to 10.0 can be incorporated. Such buffer agent are described in publications such as "Chemistry Handbook, Fundamental Edition" compiled by The Chemical Society of Japan (Maruzen Ltd., Tokyo, 1966) pages 1312–1320; "Modern Electrophoresis" editted by Aoki & Nagai (Hirokawa Shoten, 1973), pages 320–322; "Data for Biochemical Research" compiled by R. M. C. Dawson et al., second edition (Oxford at the Clarendon Press, 1969) pages 476–508; "Biochemistry" 5/-, 467 (1966); and "Analytical Biochemistry" 104, pages 300–310 (1966). Examples of the buffer agent include a buffer agent containing barbital, a buffer agent containing tris(hydroxymethyl)aminomethane (Tris), a buffer agent containing phosphate, a buffer agent containing borate, a buffer agent containing acetic acid or acetate, a buffer agent containing citric acid or citrate, a buffer agent containing lactic acid or lactate, and a buffer agent containing glycine; as well as N,N-bis(2-hydroxyethyl)glycine (Bicine), N-2-hydroxyethylpiperazine-N'-2-hydroxypropane-3-sulfonic acid (HEPPSO) or its salt, N-2-hydroxyethylpiperazine-N'-3-propanesulfonic acid (EPPS) or its salt, N-[tris(hydroymethy)methyl]-3-aminopropane-sulfonic acid (TAPS) or its salt. Preferably examples of the buffer agent include potassium dihydrogenphosphate-disodium hydrogenphosphate, Tris-sodium borate, Tris-sodium borate-EDTA·2Na, Tris-citric acid, sodium barbital-sodium acetate, sodium barbital-hydrochloric acid, barbital-sodium barbital, acetic acid-sodium acetate, lactic acid-sodium lactate, citric acid-desodium hydrogenphosphate, Bicine, HEPPSO, sodium salt of HEPPSO, EPPS, sodium salt of EPPS, TAPS, sodium salt of TAPS, etc.

In the gel membrane of the element of electrophoresis of DNA and the like, a buffer agent which is able to buffer a solution to a range of pH 8.0 to 9.0, preferably pH 8.2 to 8.3 can be incorporated. Such buffer agents are described in the aforementioned publications. Examples of the buffer agent include tris(hydroxymethyl)aminomethane (Tris), N,N-bis(2-hydroxyethyl)glycine (Bicine), N-2-hydroxyethylpiperazine-N'-2-hydroxypropane-2-sulfonic acid or its Na or K salt, N-2-hydroxyethylpiperazine-N'-2-hydroxypropane-3-sulfonic acid (HEPPSO) or its Na or K salt, N-[tris(hydroymethy)-methyl]-3-aminopropanesulfonic acid (TAPS) or its Na or K salt; as well as an acid, an alkali, and a salt employable in combination with the compounds. Preferable examples of the buffer agent include Tris, boric acid-EDTA·2Na (pH 8.3).

The gel membrane of the element of the invention is formed by radical crosslinking polymerization between the monomer such as acrylamide with the bifunctional compound (crosslinking agent) in an aqueous medium in which the water-soluble polymer and agarose preferably are dissolved almost homogeneously. Thus obtained gel is assumed to have a structure in which the water-soluble polymer and agarose are dispersed in the three dimensional crosslinked polymer formed by the reaction of the monomer and cross-linking agent, and the water-soluble polymer and agarose dispersed and entangle with the three dimensionally crosslinked polymer structure.

The crosslinking polymerization can be initiated by a known method, for instance, in the presence of a peroxide and/or under irradiation of ultra-violet rays. The reaction can be further accelerated by heat and irradiation with ultra-violet rays.

As the polymerization catalyst, a known low temperature-polymerization initiator such as those described in "Electrophoresis" 1981, 2, 213–219, ibid, 1981, 2, 220–228; and "Modern Electrophoresis" editted by Aoki & Nagai (Hirokawa Shoten, 1973) can be used. Examples of the initiator include a mixture of $\beta$-dimethylaminopropionitrile (DMAP) and ammonium peroxodisulfate, a mixture of N,N,N',N'-tetramethylethylenediamine (TEMED) and ammonium peroxidisulfate, a mixture of TEMED and riboflavin, a combination of a mixture of TEMED, riboflavin and hydrogen peroxide, and irradiation with ultra-violet rays. The radical reaction initiator can be employed in the amount of approx. 0.3 to 5 wt. %, preferably approx. 0.5 to 3 wt. %, based on the total amount of the monomer and crosslinking agent.

A polyol compound such as glycerol or ethylene glycol can be contained in the aqueous gel membrane of the element of the invention as a wetting agent. The polyol compound can be introduced in an amount of approx. 5 to 40 wt. % based on the volume of the aqueous gel membrane. Glycerol is particularly preferably among the polyol compounds. The addition of the wetting agent serves to keep the gel membrane from excessive dryness possibly caused by evaporation of water during storage of the medium, whereby preventing the medium from turning brittle or cracking caused by the excessive dryness. Thus, the improvement of physical properties of the gel membrane is accomplished.

The gel membrane of the element of the invention can be prepared by a process in which a gel forming solution is coated by a known method on an electric insulation support having the adhesive layer containing a cellulose derivative thereon. The gel forming solution is then crosslinked to polymerization on the surface of the support.

In the case of the gel forming solution is cross-linked on the surface of the support, the surface of the gel forming solution layer can be covered with a covering material such as a film, sheet, or plate. The same material as employable for the support can be employed as the covering material. The covering materials may be previously so treated by glow discharge treatment to have a hydrophilic surface. The covering material has thickness of not more than 300 μm, and preferably has approx. 4 to 200 μm, from the practical viewpoint.

In the case that the covering material is thick (e.g., approx, 70 to 300 μm), the element of the present invention can be prepared by the following steps: the gel forming solution is first coated on the covering material and crosslinked thereon to form the desired gel medium layer, and then a support having the metal oxide layer thereon is provided on the gel medium layer.

The gel membrane of the invention can be employed for the horizontal or vertical electrophoresis, disc electrophoresis, etc, by known methods described, for instance, in the aforementioned texts.

The medium for electrophoresis provided to the element of the present invention is strongly bound to the support through the provision of the specific adhesive layer. Accordingly, the element for electrophoresis of the present invention is always kept in the form of an integrated unit in the course of ordinary procedures. For this reason, the complicated procedures conventionally required in the electrophoresis of proteins, conjugated proteins, DNA, DNA cleavage products, etc. can be simplified by the use of the element for electrophoresis according to the present invention.

The present invention will be more clearly understood with reference to the following examples.

EXAMPLE 1

A surface of a cololess transparent polyethylene terephthalate sheet (thickness 180 μm) was made hydrophilic by irradiation of ultraviolet rays. On the surface of the sheet (support) was coated a coating solution containing the cellulose derivative set forth in Table 1 to have a thickness of approx. 0.5 μm (as the solid layer basis). The coated layer was dried at approx. 110° C. to give a cellulose derivative-containing layer.

TABLE 1

| (Composition of Coating Layer for Adhesive Layer) | | |
|---|---|---|
| Sample No. | Cellulose Derivative | Concentration of Coating Solution (g/100 ml solvent) |
| 1 | Nitrocellulose | 5 g. |
| 2 | Diacetylcellulose | 5 g. |
| 3 | Nitrocellulose | 2.5 g. |
|   | Diacetylcellulose | 2.5 g. |

The adhesiveness between the PET sheet (support) and the adhesive layer was evalutated by a cross-cut method. The samples No. 1 to No. 3 (according to the present invention) showed satisfactory adhesiveness.

On the adhesive layer provided on the surface of the support was formed a polyacrylamide gel membrane of 0.5 mm thick by coating an aqueous solution containing 9.5 g. of acrylamide, 0.5 g. of BIS, 3.58 g. of disodium hydrogenphosphate 12 hydrates, 0.33 g. of sodium dihydrogenphosphate 2 hydrates, and 0.10 g. of sodium dodecylsulfate (SDS) in 100 ml. volume after addition of 1.3 ml of ammonium peroxodisulfate (5 weight %) and 33 μl. of TEMED, both being the polymerization initiator. Thus, an element for electrophoresis was obtained.

The same procedure was repeated except that the provision of the adhesive layer of cellulose derivative was not provided on the support. Thus, an element for comparison consisting of the support and the polyacrylamide gel membrane thereon was prepared.

The gel membrane was pushed with a finger to examine the adhesiveness between the gel layer and the support. The Samples No. 1 to No. 3 according to the invention showed satisfactory adhesiveness, while the comparison sample was not satisfactory in the adhesion.

EXAMPLE 2

A PET sheet having an adhesive layer of the same cellulose derivative as in Table 1 of Example 1 was prepared. On the adhesive layer was formed a polyacrylamide gel membrane of 0.5 mm thick by coating an aqueous solution containing 9.5 g. of acrylamide, 0.5 g. of BIS, 0.3 g. of agarose 1600, 2.5 g. of polyacrylamide, 3.56 g. of disodium hydrogenphosphate 12 hydrates, 0.33 g. of sodium dihydrogenphosphate 2 hydrates, and 0.10 g. of sodium dodecylsulfate (SDS) in 100 ml. volume after addition of 1.3 ml of ammonium peroxodisulfate (5 wt. %) and 33 μl. of TEMED, both being the polymerization initiator. Thus, elements for electrophoresis (Samples 1 to 3) were obtained.

A comparison sample was further obtained by forming the polyacrylamide gel membrane directly on the PET sheet.

A control(standard) protein was electrophoresed on the polyacrylamide gel membrane. The element was then immersed in an aqueous Coomasie Blue R-250 (Colour Index Constitution Number 42660) solution (0.1 %) for dyeing. In the dyeing process, the adhesiveness between the support and the polyacrylamide gel membrane was observed.

The gel membrane of the comparison sample completely separated immediately after the element was immersed in the dyeing solution.

The gel membranes of the Samples No. 1 to No. 3 (according to the present invention) were completely bound to the supports during the dyeing process. No unsatisfactory results were observed in the electrophoresis in the use of said element.

EXAMPLE 3

On the adhesive layer of the same cellulose derivative as in Table 1 of Example 1 provided on a PET sheet was formed a polyacrylamide gel membrane in the same manner as in Example 2. Thus, there were prepared three samples (Samples No. 1 to No. 3). Further, a comparison sample was prepared in the same manner as in Example 2.

The gel membrane as well as the support was cut simultaneously to observe the cut face (section) of the gel membrane. The gel membrane of the comparison sample separated in part from the support, while all of the Samples No. 1 to No. 3 showed satisfactory adhesiveness. Accordingly, it was confirmed that the samples of the invention were cut in the form of a composite with the support.

EXAMPLE 4

On the adhesive layer of the same cellulose derivative as in Table 1 of Example 1 provided on a PET sheet was formed a polyacrylamide gel membrane of 1 mm thick by coating an aqueous solution containing 4.56 g. of acrylamide, 0.24 g. of BIS, 1.2 g. of polyacrylamide, 0.3 g. of agarose, 1.08 g, of tris(hydroxymethyl)aminomethane [CAS Registry No. 77-86-1], 0.55 g. of boric acid, 93 mg of EDTA·Na salt and 20 g. of glycerol in 100 ml. volume after addition of 1.3 ml of ammonium peroxodisulfate (5 weight %) and 33 µl. of TEMED, both being the polymerization initiator, and causing the polymerization reaction in a nitrogen atmosphere. Thus, an element for electrophoresis was obtained.

Plasmid pBR-322 of *Escherichia coli* was treated by a restriction enzyme AsuI and then resolved on the gel membrane of the above element. The DNA resolved pattern on the membrane which were visualized by dyeing was confirmed to be normal.

The cutting of the end of the gel membrane for the formation of a sample inlet was performed smoothly and give a square inlet. Moreover, the resolved DNA bands were collected accurately.

EXAMPLE 5

On the adhesive layer of the same cellulose derivative as in Table 1 of Example 1 provided on the surface of the PET support was formed a polyacrylamide gel membrane of 0.5 mm thick by coating an aqueous solution containing 11.87 g. of acrylamide, 630 mg. of BIS, 42 g. urea, 1.08 g. of tris(hydroxymethyl)aminomethane [CAS Registery No. 77-86-1], 0.55 g. of boric acid, 93 mg of EDTA·Na salt and 20 g. of glycerol in 100 ml. volume after addition of 1.3 ml of ammonium peroxodisulfate (5 wt. %) and 33 µl. of TEMED, both being the polymerization initiator. Thus, an element for electrophoresis was obtained.

The same procedure was repeated except that the provision of the adhesive layer of cellulose derivative was not provided on the support. Thus, an element for comparison consisting of the support and the polyacrylamide gel membrane thereon was prepared.

The gel membrane was pushed with a finger to examine the adhesiveness between the gel layer and the support. The samples according to the invention showed satisfactory adhesiveness, while the comparison sample was not satisfactory in the adhesion.

EXAMPLE 6

On the adhesive layer of the same cellulose derivative as in Table 1 of Example 6 provided on the surface of the PET sheet was formed a polyacrylamide gel membrane of 0.5 mm thick by coating an aqueous solution containing 11.87 g. of acrylamide, 630 mg. of BIS, 42 g. of urea, 0.3 g. of agarose, 1.08 g. of tris(hydroxymethyl)aminomethane [CAS Registry No. 77-86-1], 0.55 g. of boric acid, and 93 mg of EDTA·Na salt in 100 ml. volume after addition of 1.3 ml of ammonium peroxodisulfate (5 wt. %) and 33 µl. of TEMED, both being the polymerization initiator. Thus, three elements for electrophoresis were obtained.

A comparison sample was further obtained by forming the polyacrylamide gel membrane directly on the PET sheet.

A sample ($^{32}$P-DNA) cleaved by Maxam-Gilbert method) was electrophoresed on the polyacrylamide gel membrane for sequencing the DNA. After the electrophoresis was complete, the element was immersed in an aqueous acetic acid (10%) solution for removing urea and fixing the DNA. The gel membrane was dried and subjected to the conventional autoradiographic process.

The gel membrane of the comparison sample completely separated immediately after the element was immersed in the aqueous acetic acid (10%) solution.

The gel membranes of the samples according to the present invention were completely bound to the supports in the solution. No unsatisfactory results were observed in the electrophoresis in the use of said elements.

EXAMPLE 7

On the adhesive layer of the same cellulose derivative as in Table 1 of Example 1 provided on a PET sheet was formed a polyacrylamide gel membrane in the same manner as in Example 6. Thus, there were prepared three samples. Further, a comparison sample was prepared in the same manner as in Example 6.

The gel membrane as well as the support was cut simultaneously to observe the cut face (section) of the gel membrane. The gel membrane of the comparison sample separated in part from the support, while all of the samples of the invention showed satisfactory adhesiveness. Accordingly, it was confirmed that the samples of the invention were cut in the form of a composite with the support.

We claim:

1. An element for electrophoresis comprising:
   (I) a plastic material support;
   (II) an adhesive layer containing not less than 80 wt. percent of a cellulose derivative selected from the group consisting of diacetyl cellulose, triacetyl cellulose and nitrocellulose; and
   (III) a medium layer for electrophoresis comprising an aqueous polyacrylamide gel formed by crosslinking polymerization of an acrylamide compound and a crosslinking agent in the presence of water, which are superposed in this order.

2. The element for electrophoresis as claimed in claim 1 in which said adhesive layer consists essentially of said cellulose derivative.

3. The element for electrophoresis as claimed in claim 1 or 2 in which the plastic material sheet is a polyethylene terephthalate sheet.

4. The element for electrophoresis as claimed in claim 1 or 2 in which said medium layer contains a water-soluble polymer and agarose.

5. The element for electrophoresis as claimed in claim 1 or 2 in which said medium layer contains an anionic surfactant.

6. The element for electrophoresis as claimed in claim 5 in which said anionic surfactant is an alkylsulfate.

7. The element for electrophoresis as claimed in claim 6 in which said alkylsulfate is sodium dodecylsulfate.

8. The element for electrophoresis as claimed in claim 1 or 2 in which said medium layer contains a compound having at least one carbamoyl group.

9. The element for electrophoresis as claimed in claim 8 in which said compound having at least one carbamoyl group is urea or formamide.

* * * * *